United States Patent
Bannwart (10) Patent No.: US 11,291,588 B2
(45) Date of Patent: Apr. 5, 2022

(54) POROUS WOUND DRESSING FOR USE IN NEGATIVE-PRESSURE THERAPY

(71) Applicant: MEDELA HOLDING AG, Baar (CH)

(72) Inventor: Lukas Bannwart, Rotkreuz (CH)

(73) Assignee: MEDELA HOLDING AG, Baar (CH)

( * ) Notice: Subject to any disclaimer, the term of this patent is extended or adjusted under 35 U.S.C. 154(b) by 158 days.

(21) Appl. No.: 16/467,914

(22) PCT Filed: Jan. 16, 2018

(86) PCT No.: PCT/EP2018/050916
§ 371 (c)(1),
(2) Date: Jun. 7, 2019

(87) PCT Pub. No.: WO2018/134162
PCT Pub. Date: Jul. 26, 2018

(65) Prior Publication Data
US 2019/0336345 A1      Nov. 7, 2019

(30) Foreign Application Priority Data

Jan. 23, 2017    (EP) .................................... 17152672

(51) Int. Cl.
*A61F 13/00*        (2006.01)
*A61F 13/02*        (2006.01)
(Continued)

(52) U.S. Cl.
CPC .... *A61F 13/00068* (2013.01); *A61F 13/0216* (2013.01); *A61F 13/148* (2013.01);
(Continued)

(58) Field of Classification Search
CPC ............ A61F 13/00068; A61F 13/0216; A61F 13/148; A61F 13/00063;
(Continued)

(56) References Cited

U.S. PATENT DOCUMENTS 4,233,969 A    11/1980    Lock et al.
4,664,662 A     5/1987    Webster
(Continued)

FOREIGN PATENT DOCUMENTS

EP    2538902 A1    1/2013
EP    2567682 A1    3/2013
(Continued)

OTHER PUBLICATIONS https://en.wikipedia.org/wiki/Perforation accessed on Mar. 3, 2021.*
(Continued)

*Primary Examiner* — Philip R Wiest
*Assistant Examiner* — Gregory J Feulner
(74) *Attorney, Agent, or Firm* — Marshall, Gerstein & Borun LLP (57) ABSTRACT

A porous wound dressing for use in negative-pressure therapy is proposed. The wound dressing has an outer edge which defines a substantially oval or rectangular outer shape of the wound dressing with a major axis and a minor axis. The wound dressing has one or more incisions or perforations which together form one or more arc-shaped lines and serve for cutting the wound dressing to size in order to adapt the wound dressing to the shape and/or size of a wound. The one or more arc-shaped lines each extend asymmetrically with respect to the major axis and/or to the minor axis and each enclose, together with a portion of the outer edge, a segment of the wound dressing that is designed for separation from the wound dressing.

17 Claims, 5 Drawing Sheets

(51) Int. Cl.
*A61F 13/14* (2006.01)
*A61M 1/00* (2006.01)
*A61M 27/00* (2006.01)

(52) U.S. Cl.
CPC ......... *A61M 1/90* (2021.05); *A61F 13/00063* (2013.01); *A61F 2013/0054* (2013.01); *A61F 2013/00174* (2013.01); *A61F 2013/00536* (2013.01); *A61F 2013/00855* (2013.01); *A61M 27/00* (2013.01); *A61M 2210/1021* (2013.01)

(58) Field of Classification Search
CPC .. A61F 2013/00174; A61F 2013/00536; A61F 2013/0054; A61F 2013/00855; A61M 1/0088; A61M 27/00; A61M 2210/1021
See application file for complete search history.

(56) References Cited

U.S. PATENT DOCUMENTS

| | | | |
|---|---|---|---|
| 4,699,134 A | 10/1987 | Samuelsen | |
| 5,264,218 A | 11/1993 | Rogozinski | |
| 7,354,211 B2* | 4/2008 | Ahne | B26D 5/08 346/24 |
| D838,374 S | 1/2019 | Bannwart | |
| D841,172 S | 2/2019 | Bannwart | |
| 2009/0099519 A1 | 4/2009 | Kaplan | |
| 2011/0213287 A1* | 9/2011 | Lattimore | A61F 13/00068 602/46 |
| 2012/0253302 A1 | 10/2012 | Corley | |
| 2014/0363605 A1* | 12/2014 | Ogawa | C09J 7/21 428/43 |

FOREIGN PATENT DOCUMENTS

| | | |
|---|---|---|
| WO | WO-2011106722 A1 | 9/2011 |
| WO | WO-2012069167 A1 | 5/2012 |
| WO | WO-2012106590 A2 | 8/2012 |
| WO | WO-2014170461 A1 | 10/2014 |
| WO | WO-2015000610 A1 | 1/2015 |
| WO | WO-2016014645 A1 | 1/2016 |

OTHER PUBLICATIONS

International Search Report for Application No. PCT/EP2018/050916, dated Feb. 27, 2018.
Design U.S. Appl. No. 29/671,043, filed Nov. 21, 2018.
Design U.S. Appl. No. 29/671,745, filed Nov. 29, 2018.
Swiss Registration No. 142962, registered on Feb. 10, 2017.

* cited by examiner

POROUS WOUND DRESSING FOR USE IN NEGATIVE-PRESSURE THERAPY

CROSS-REFERENCE TO RELATED APPLICATION

This present application is the US national phase of International Patent Application No. PCT/EP2018/050916, filed Jan. 16, 2018, which claims priority to European Application No. 17152672.6, filed Jan. 23, 2017. The priority application, EP 17152672.6, is hereby incorporated by reference in its entirety.

TECHNICAL FIELD

The present invention relates to a porous wound dressing for use in negative-pressure therapy, in particular for the treatment of abdominal wounds, and to a wound cover set that comprises a wound dressing of this kind.

PRIOR ART

It is known for large or poorly healing wounds to be treated using a negative-pressure drainage device. The wound is covered by a covering, for example a film or a stiff hood, such that a wound cavity is obtained. A drainage hose, which is connected to a negative-pressure pump, is inserted from the outside into the wound cavity in order to aspirate wound secretions from the wound. In order to fill the wound cavity and, in particular, in order to distribute the negative pressure uniformly across the wound surface, a wound dressing is applied to the wound. This wound dressing usually has a foam inlay with suitably formed pores. The foam inlay also usually serves as an absorption body for the wound secretions and accordingly has to be changed frequently. A liquid-permeable wound-side contact sheet, which lies directly on the wound, is in most cases also provided between the wound and the foam inlay.

Corresponding wound dressings are known, for example, from U.S. Pat. Nos. 4,233,969, 4,664,662 and WO 2012/069167.

In order to adapt the foam inlay to the size and shape of the wound, it is customary for the physician or medical personnel to cut it to a suitable size prior to treatment, for example by means of sterile scissors. However, this cutting can result in frayed edges, which can lead to foam particles coming loose from the wound dressing. There is a danger that foam particles released in this way from the wound dressing will remain in the wound and have to be removed with some difficulty after completion of the negative-pressure therapy.

To make it easier to cut the wound dressing to size and to avoid frayed edges of this kind, it is known to provide clean incisions or perforations in the wound dressing. The incisions or perforations are provided in such a way that the wound dressing can be cut to different sizes with their assistance.

For example, US 2009/0099519 and U.S. Pat. No. 5,264,218 disclose wound dressings that can be cut to a desired size with the aid of several concentric circles of incisions or perforations.

U.S. Pat. No. 4,699,134 and EP 2 538 902 disclose wound dressings with ellipsoid and/or radial incisions or perforations, which likewise serve for cutting the wound dressing to size.

It is desirable to reduce as far as possible the particles coming loose from the wound dressing. It is also found in practice that the wound dressings are not always cut and are instead simply torn apart from each other at the perforation bridges. It is therefore desirable to minimize the number of cuts that have to be made to cut the wound dressing to size.

SUMMARY OF THE INVENTION

It is an object of the invention to make available a wound dressing that can be adapted to a wound easily and with the fewest possible cuts.

In order to achieve this object, the present invention proposes a wound dressing for use in negative-pressure therapy of wounds, in particular for the treatment of abdominal wounds, wherein the wound dressing has an outer edge which defines in particular a substantially oval or rectangular outer shape of the wound dressing with a major axis and a minor axis, wherein the wound dressing has one or more incisions or perforations which together form one or more arc-shaped lines and serve for cutting the wound dressing to size in order to adapt the wound dressing to the shape and/or size of a wound. The one or more arc-shaped lines each extend asymmetrically with respect to the major axis and/or to the minor axis and each enclose, together with a portion of the outer edge, a segment of the wound dressing that is designed for separation from the wound dressing and for subsequent use in the negative-pressure therapy of wounds.

A substantially oval or rectangular outer shape means that the outer shape does not necessarily have to be exactly oval or rectangular in the geometric sense, but rather can also slightly deviate therefrom. The observer, however, should be able to readily recognize the oval or rectangular outer shape despite these possible slight deviations. Thus, in the case of a substantially rectangular outer shape, the corners can for example also be slightly rounded or deviations within production-related tolerances can be present.

Since the one or more arc-shaped lines extend asymmetrically with respect to the major axis and/or to the minor axis and additionally enclose, together with a portion of the outer edge of the wound dressing, a segment that can be separated and used for the negative-pressure therapy, it is possible to reduce the number of cuts that are needed to cut the wound dressing to size. It has been found that cut surfaces obtained when producing the wound dressing by means of punching result in much less fraying of the edges and far fewer detached particles than in the case of cut surfaces that are obtained by cutting by means of scissors. Since the portion of the outer edge of the wound dressing also forms part of the outer edge of the segment, the length of the corresponding arc-shaped line along which the segment is connected to the rest of the wound dressing decreases. Accordingly, fewer connections (bridge portions) are also needed in order to connect the segment to the rest of the wound dressing along this arc-shaped line. The physician or the medical personnel therefore have to make fewer cuts in order to adapt the wound dressing to the wound. Since fewer cuts are needed, the number of particles arising from adapting the wound dressing to the wound is reduced. Moreover, the punching work during production is reduced.

The term "oval" signifies a plane and rounded convex contour which, in the broadest sense, is akin to the profile of a bird's egg. Circles and ellipses are included here as special cases, in contrast to which any desired oval does not need to have an axis of symmetry.

The rectangular shape also includes, as a special case, square shapes. If the wound dressing has a rectangular outer shape, the corner areas are preferably each rounded.

The major axis is to be regarded as the axis along which the outer shape of the wound dressing has its greatest lengthwise extent. In the case of an oval shape and in particular an ellipsoid shape, the major axis extends through the two foci.

The minor axis is generally to be regarded as the axis along which the outer shape of the wound dressing perpendicular to the major axis has its greatest lengthwise extent. Thus, the minor axis is perpendicular to the major axis. In the case of an ellipse, the minor axis extends through the midpoint arranged centrally between the two foci. In some embodiments, the major axis and the minor axis can also be of the same length, as is the case, for example, in a wound dressing with a circular outer shape.

The wound dressing usually has a constant thickness perpendicular to the surface spanned by the major axis and the minor axis. The incisions or perforations can in each case extend through only part of the thickness of the wound dressing. However, they in each case preferably extend all the way through the wound dressing.

The observations regarding symmetry in each case relate to the axial symmetry with respect to the correspondingly cited major axis or minor axis. The whole arc-shaped line along its entire longitudinal extent is to be considered in each case.

After the segment has been separated from the wound dressing, it can generally and preferably be used directly for wound therapy without any further modifications, in particular without any further cutting to size. The segment preferably has an outer contour composed exclusively of contour portions which are each formed constantly, that is to say have a continuous arc-shaped profile without any corners or kinks. Advantageously, the portions of the outer contour are moreover each continuously convex. More preferably, the segment has an outer contour which even as a whole is formed constantly and is continuously convex.

Preferably, the segments enclosed by in each case one arc-shaped line and one portion of the outer edge are each arranged asymmetrically with respect to the first and/or to the second axis. Optionally, additional segments delimited by one or more arc-shaped lines may be present which that are not delimited by a portion of the outer edge and/or which do not have to be arranged asymmetrically with respect to the first and/or to the second axis.

Along their entire lengthwise extent, the arc-shaped lines each preferably have a constant profile, that is to say a profile having no corners. The risk of particles coming loose is thereby reduced.

The wound dressing is preferably made from a foam, in particular from an open-cell, reticulated foam. The material can in particular be polyurethane ether. However, the use of polyurethane ester or polyvinyl alcohol is also possible. The wound dressing can have antimicrobial silver particles and/or odour-inhibiting hydrocolloid, for example cyclodextrin. Generally, the wound dressing is liquid-permeable at least in one direction and is preferably dimensionally stable.

The outer shape of the segment or the outer shapes of the segments preferably correspond substantially in each case to the outer shape of the wound dressing. Except for the dimensions, the outer shape of the segment or the outer shapes of the segments are thus in each case configured to correspond substantially to the outer shape of the wound dressing. In other words, the observer is able to readily recognize the outer shape of the wound dressing in the outer shapes of the segments. For the recognition, the outer shapes of the segments do not have to be identical (with the exception of the dimensioning) to the outer shape of the wound dressing, but it is sufficient, if the outer shapes of the segments substantially correspond to the outer shape of the wound dressing in each case. If for example the wound dressing has asymmetrical, oval outer shape or an asymmetrical, angular outer shape, then a symmetrical, oval outer shape or an asymmetrical, angular outer shape is in each case also readily recognizable with respect to the segments. Advantageously, the outer shapes of the segments in each case substantially correspond such to the outer shape of the wound dressing, that the wound dressing can in each case imaginary be overlaid such with the segments, if their dimensioning is suitably adapted without changing the aspect ratios, that at least 80%, preferably 90%, more preferably 95% of the surface areas of the respective segment and of the wound dressing in its original shape and dimension overlap each other or are nearly congruent. In this way, the wound dressing can thus be made smaller, and adapted to the size of the wound, without substantially changing its outer shape. Therefore, the one or more segments preferably likewise have a substantially oval or rectangular outer shape.

Bridge portions are usually provided which are each arranged between the incisions or perforations in order to separate these from one another within the respective arc-shaped line, or which are each arranged at the end points of the one or more arc-shaped lines, in order to separate the incisions or perforations there from the outer edge of the wound dressing.

The bridge portions each have a length extending along the lengthwise extent of the arc-shaped line, which length is preferably many times shorter than the total length of the respective arc-shaped line. More preferably, the length of the bridge portions is even many times shorter than the individual incisions or perforations of the corresponding arc-shaped line. The bridge portions thus preferably have a much smaller length compared to the incisions or perforations. The cut surface can thereby be minimized.

The lengths of all the bridge portions extending along the lengthwise extent of an arc-shaped line, and serving to connect a respective segment to the rest of the wound dressing, preferably differ from one another by at most four times, more preferably by at most double. In other words, all the bridge portions of an arc-shaped line thus preferably have similar lengths. Most preferably, all the bridge portions serving to connect a respective segment to the rest of the wound dressing have approximately the same length.

The cut surface can be further minimized if the wound dressing in the area of the bridge portions is made less thick, preferably at most half as thick, as in the other areas.

The bridge portions are preferably each arranged at regular intervals along the one or more arc-shaped lines. In this way, a good connection of the one or more segments to the rest of the wound dressing can be achieved using a minimum number of bridge portions.

Advantageously, the one or more arc-shaped lines, together with the corresponding portion of the outer edge, each enclose the respective segment completely or at least substantially completely. That is to say, the one or more arc-shaped lines each extend substantially from a first part of the outer edge of the wound dressing as far as a second part of the outer edge of the wound dressing. In other words, the arc-shaped lines thus extend from edge to edge across the entire wound dressing.

To allow the wound dressing to be cut to a large number of sizes, a plurality of such arc-shaped lines are preferably provided. Many possible ways of cutting the wound dressing to size, in order to obtain segments of similar shape but of different sizes, can be achieved if the plurality of arc-shaped lines extend at least approximately parallel to one another. The arc-shaped lines are advantageously arranged at regular intervals from one another.

The one or more arc-shaped lines preferably each extend asymmetrically with respect to the major axis and intersect the minor axis, or they extend asymmetrically with respect to the minor axis and intersect the major axis.

In a particularly preferred embodiment, the one or more arc-shaped lines each extend symmetrically with respect to the minor axis or to the major axis and each extend at least approximately parallel to a further portion of the outer edge of the wound dressing. A mussel-shaped division of the wound dressing into segments is thus obtained. A division of the wound dressing into segments can be obtained in which particularly few cuts are needed to adapt the wound dressing, yet in which many possible ways of adapting the wound dressing are provided. The crescent-shaped elements that generally result from this division of the wound dressing can be broad and thus have a stable configuration.

According to a development of the invention, at least a first of the arc-shaped lines extends symmetrically with respect to the minor axis or to the major axis and extends at least approximately parallel to a first further portion of the outer edge of the wound dressing, and a second of the arc-shaped lines extends symmetrically with respect to the minor axis or to the major axis and extends at least approximately parallel to a second further portion of the outer edge of the wound dressing, which second further portion lies radially opposite the first further portion. In this embodiment, the first arc-shaped line and the second arc-shaped line are thus curved in opposite directions. Moreover, the first arc-shaped line and the second arc-shaped line advantageously intersect at two intersection points. Additional possibilities for cutting the wound dressing to size can be provided in this way, one of these additional possibilities being provided, for example, by the segment located between the two intersection points.

According to another development of the invention, at least a first of the arc-shaped lines extends symmetrically with respect to the minor axis, and at least a second of the arc-shaped lines extends symmetrically with respect to the major axis. In this way, it is possible to achieve a still greater number of possibilities for cutting the wound dressing to size into segments that are of different dimensions but also of different shapes. Advantageously, this can be achieved in particular if the at least second of the arc-shaped lines does not intersect the minor axis.

According to yet another development of the invention, the one or more arc-shaped lines each extend asymmetrically with respect to the major axis and also asymmetrically with respect to the minor axis. In this way, the physician or the medical personnel can be provided with a large number of possible ways of cutting the wound dressing to size, and the number of cuts required can be further reduced at the same time. Advantageously, the arc-shaped lines extend at least approximately parallel to one another, resulting in a mussel-shaped division of the wound dressing into segments.

Two lines extend approximately parallel to one another, if they still appear, at least at first glance in the eye of the observer, as nearly parallel to each other. An exact parallelism of both lines in a geometric sense is not necessary for this purpose. For example, circular arc-shaped lines are also regarded to be nearly parallel to each other, if they have a similar radius and a not too different position of the center point, i.e. if for example the radii of the lines differ by less than 10%, preferably less than 5%, from each other and their center points are distant from each other by a distance of less than 10%, preferably less than 5%, of the radius. The same applies correspondingly for a line that extends at least approximately parallel to a portion of the outer edge of the wound dressing.

In certain embodiments, at least one arc-shaped line can be provided which is formed by one or more incisions or perforations in the wound dressing and which on its own, or together with a portion of the outer edge of the wound dressing or together with one or more of the other arc-shaped lines, forms substantially a circle. With the expression "forms substantially a circle" is meant that the shape, for example due to production-related tolerances, can also slightly deviate from an exact circle in the geometric sense, as long as, however, it is still recognizable as a circle for the observer at first glance. It has been found that a circular configuration of a segment is often best, especially if the wound dressing has to be cut to a relatively small size.

The present invention also relates to a wound cover kit for use in negative-pressure therapy of wounds, having
  a wound-side contact sheet designed to be placed directly on a wound;
  a porous wound dressing, which is designed as described above; and
  a covering which serves to cover and seal off the wound area from the outside.

The wound cover kit can additionally comprise a hose unit, which serves to connect the wound cavity to a suction unit.

The wound-side contact sheet can be made of polyurethane, for example. The covering is advantageously transparent and can, for example, by made of acrylic. The covering can in particular be in the form of one or more adhesive films. The connection of the wound cavity to the vacuum pump can be provided, for example, by means of an attachment element which protrudes all the way through the cover or extends underneath the latter into the wound cavity, and a hose unit connecting the attachment element and the vacuum pump.

BRIEF DESCRIPTION OF THE DRAWINGS

Preferred embodiments of the invention are described below with reference to the drawings, which are provided only for explanatory purposes and are not to be interpreted as limiting the invention. In the drawings:

FIG. 2b shows a plan view of the wound dressing from FIG. 2a;

DESCRIPTION OF PREFERRED EMBODIMENTS

Figure 1:
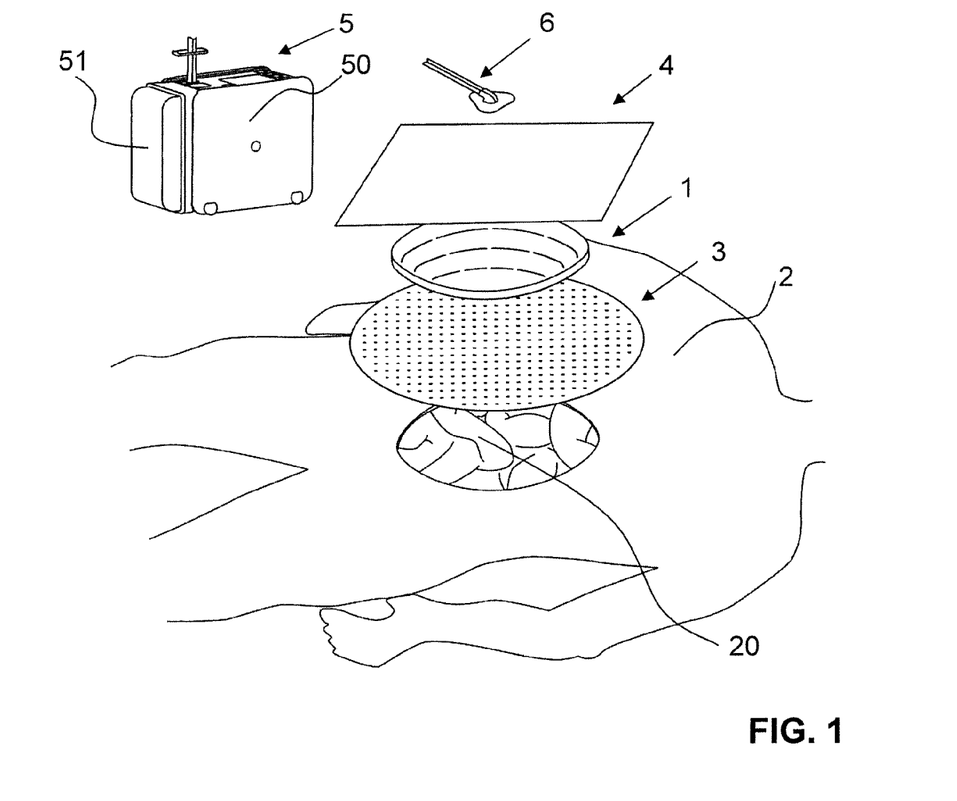
FIG. 1 shows a schematic illustration of a system with a wound cover kit according to the invention for negative-pressure therapy of an abdominal wound.

FIG. 1 shows a system for negative-pressure therapy of an abdominal wound by means of a wound cover kit according to the invention.

As can be seen in FIG. 1, the wound cover kit has a wound-side contact sheet 3, a wound dressing 1 and a covering 4. The liquid-permeable wound-side contact sheet 3, which is made of polyurethane for example, is cut to size for adaptation to the wound 20 and is then placed directly into the wound bed of a wound 20, such that it contacts the underlying body tissue of the patient 20. The wound dressing 1 is liquid-permeable at least in the direction of the covering 4 and preferably has substantial dimensional stability. It serves to fill the wound cavity of the wound 20 and is arranged in the space delimited by the wound-side contact sheet 3 and the covering 4. The covering 4, made of an airtight material, for example acrylic, is used to cover the wound cavity and seal the latter off in an airtight manner from the outside. The covering 4 is preferably in the form of one or more adhesive films.

To produce a negative pressure in the wound cavity of the wound 20, a patient-side attachment element of a hose unit 6 is routed at least partially through the covering 4 or under the latter, such that the hose unit 6 opens into the wound cavity via the attachment element. An attachment element of the hose unit 6 towards the suction pump is coupled to a suction unit 5, such that a suction pump assembly 50 of the suction unit 5 is able to generate a negative pressure in the wound cavity of the wound 20, below the covering 4, via the hose unit 6. The fluids aspirated through the hose unit 6 from the wound cavity are collected in a fluid collection container 51 mounted on the suction pump assembly 50.

The hose unit 6 can have one or more hoses, in particular two hoses. It is also possible in particular to provide an individual but double-lumen hose. The hose unit 6 preferably forms a secretion line through which the fluids are aspirated from the wound cavity, and also an auxiliary line extending parallel thereto. By means of the auxiliary line, it is possible, if need be, to flush the secretion line and/or to measure the pressure in the secretion line. For this purpose, the auxiliary line preferably opens into the secretion line in proximity to the wound 20.

The wound dressing 1 is generally made from a foam, in particular from an open-cell, reticulated foam. The material of the wound dressing 1 can in particular be polyurethane ether, although it can also be polyurethane ester or polyvinyl alcohol. The wound dressing 1 can have antimicrobial silver particles and/or odour-inhibiting hydrocolloid, for example cyclodextrin.

FIGS. 2a to 10 show various embodiments of wound dressings 1 according to the invention which each have a large number of incisions 12. Features having the same effect and/or function or having a similar effect and/or function are each provided with the same reference signs in the various embodiments.

The embodiments and variants thereof shown in FIGS. 2a to 10 differ from one another exclusively in terms of the number and/or the arrangement of the incisions 12. First of all, therefore, the basic configuration of the wound dressing 1 is explained below on the basis of FIGS. 2a and 2b, which configuration is identical in all of the embodiments shown in FIGS. 2a to 10, except for the stated number and/or arrangement of the incisions 12. The different patterns formed by the incisions 12 in the various embodiments in FIGS. 2a to 10 are then discussed.

Figure 2A:
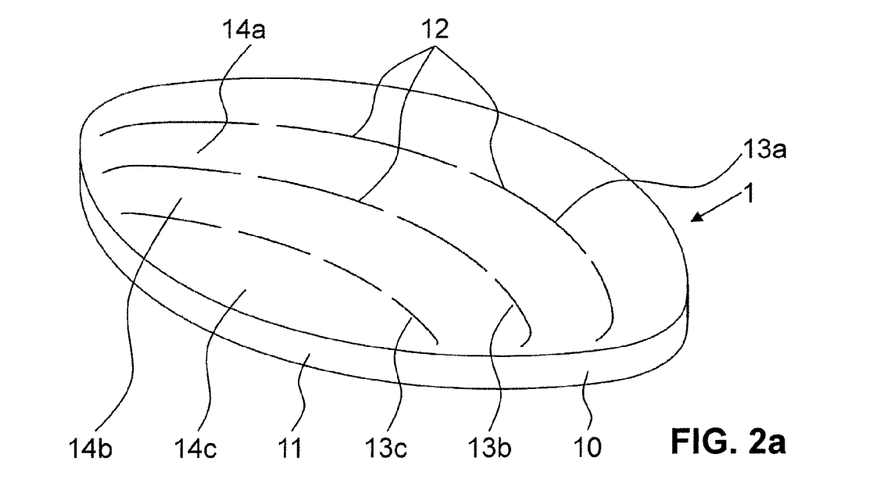
FIG. 2a shows a perspective view of a wound dressing in a first embodiment according to the invention.
Figure 2B:
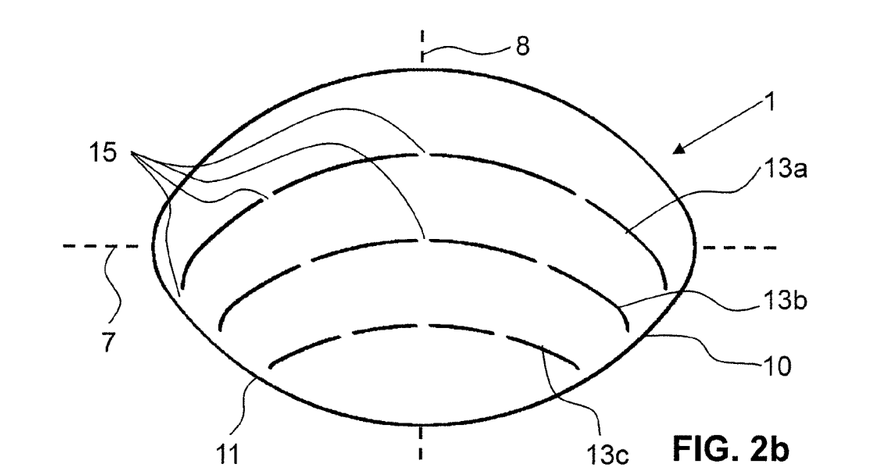

The basic configuration of the wound dressing 1 can be seen clearly in FIGS. 2a and 2b.

The wound dressing 1 has a lateral outer edge 10, which defines a long oval, almost ellipsoid shape. The wound dressing 1 has a constant thickness.

As can be clearly seen in FIG. 2b in particular, a major axis 7 and a minor axis 8 of the oval shape are defined by the outer edge 10 of the wound dressing 1. The major axis 7 corresponds to the axis along which the wound dressing 1 has its greatest longitudinal extent. The minor axis 8 corresponds to the axis along which the wound dressing 1 has its greatest longitudinal extent perpendicular to the major axis 7. In the present case, the major axis 7 and the minor axis 8 each form an axis of symmetry of the wound dressing 1. The thickness of the wound dressing 1 extends perpendicular to the plane spanned by the major axis 7 and the minor axis 8 and is identical at all points of the wound dressing 1. The thickness is many times smaller than the longitudinal extent of the wound dressing 1 along the minor axis 8.

The wound dressing 1 has a large number of incisions 12 which each extend continuously and in the same direction through the wound dressing 1, which is perpendicular on the plane spanned by the major axis 7 and the minor axis 8. The incisions 12 are pre-punched in the wound dressing 1 and serve the purpose of making it easier for the physician or the medical personnel to cut the wound dressing 1 to size in order to adapt it to the size and/or the shape of the wound 20. When cutting the wound dressing 1 to size, no cuts have to be made along each of the incisions 12, and instead only a few bridge portions 15 have to be severed which are arranged between the incisions 12 or between the outer edge 10 and one of the incisions 12. Since no cuts need to be made along the incisions 12, the danger of particles detaching in these areas is reduced to a minimum.

A plurality of incisions 12 in each case together form an arc-shaped line 13a, 13b or 13c. The arc-shaped lines 13a, 13b and 13c each extend along the longitudinal direction of the incisions 12 from a first part or portion of the edge 10 as far as a second part or portion of the edge 10.

With respect to the minor axis 8 of the wound dressing 1, all the arc-shaped lines 13a, 13b and 13c are arranged (axially) symmetrically in the embodiment shown in FIGS. 2a and 2b. The minor axis 8 is in this case crossed by all the arc-shaped lines 13a, 13b and 13c. By contrast, with respect to the major axis 7, all of the arc-shaped lines 13a, 13b and 13c are arranged asymmetrically. Moreover, the arc-shaped lines 13a, 13b and 13c each extend at least approximately parallel to one another and to the portion of the outer edge 10 arranged at the top of FIG. 2b and crossing the minor axis 8.

Each of the arc-shaped lines 13a, 13b and 13c has four incisions 12, which are separated from one another by three bridge portions 15 arranged between them. The incisions 12 arranged at the end of the arc-shaped lines 13a, 13b and 13c are each separated from the outer edge 10 by a further bridge portion 15.

By cutting the five bridge portions 15 along one of the arc-shaped lines 13a, 13b or 13c, a segment 14a, 14b or 14c can easily be separated from the rest of the wound dressing 1 by the physician or by the medical personnel. The segment 14c then represents a sub-segment of the segments 14b and 14a, and the segment 14b represents a sub-segment of the segment 14a. The outer shapes of the segments 14a, 14b and 14c correspond substantially to the outer shape of the entire wound dressing 1 in each case. The wound dressing 1 can thus be adapted quickly and easily to the size of the wound 20 by means of only five small cuts.

The segments 14a, 14b and 14c are each delimited on the one hand by the arc-shaped lines 13a, 13b and 13c and on the other hand by an edge portion 11 of the outer edge 10. Since at least part of the edge of each of the segments 14a, 14b and 14c is formed by an edge portion 11 of the outer edge 10, fewer cuts are needed to cut the wound dressing 1 to size. FIG. 2a clearly shows the mussel-shaped division of the wound dressing 1 resulting from the arc-shaped lines 13a, 13b and 13c.

The division of the wound dressing 1 by means of the arc-shaped lines 13a, 13b and 13c results in a plurality of crescent-shaped elements which are arranged back to back along the minor axis 8 and which each have a comparatively long length in relation to the longitudinal extent of the wound dressing 1 along the major axis 7. The form and arrangement of these crescent-shaped elements, in combination with their length, has the effect that the entire wound dressing 1 has a stable shape, despite the incisions 12, and is therefore easy to handle.

Figure 2C:
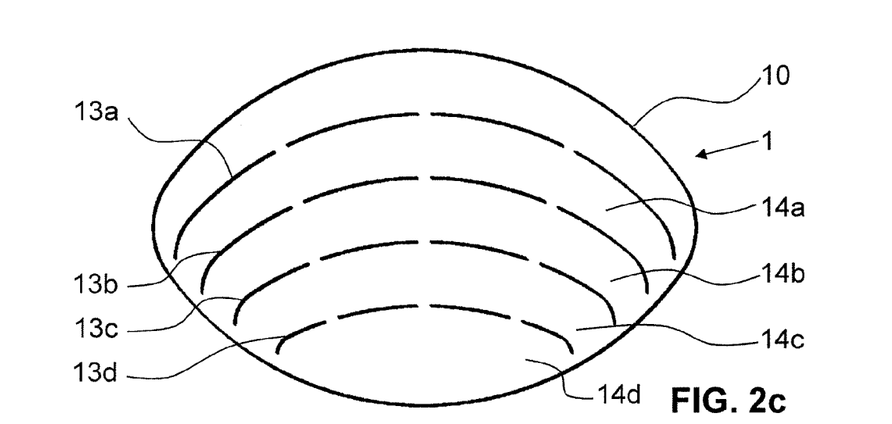
FIG. 2c shows a plan view of a wound dressing in a first variant of the first embodiment according to the invention.
Figure 2D:
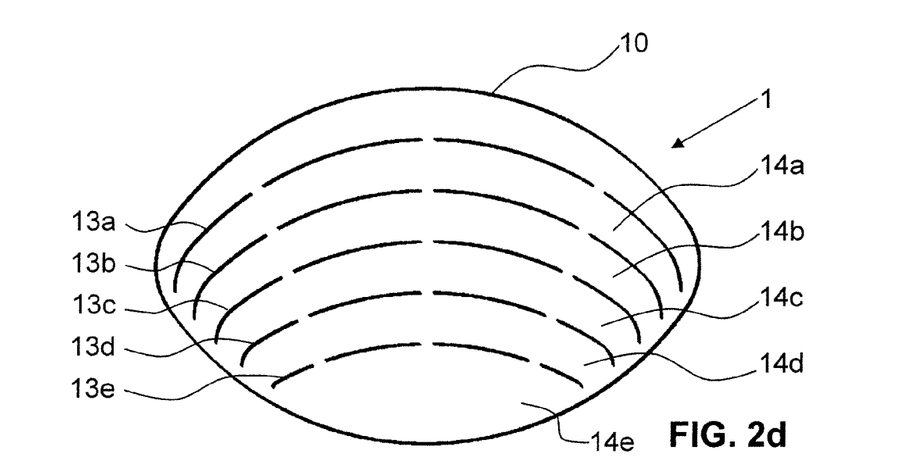
FIG. 2d shows a plan view of a wound dressing in a second variant of the first embodiment according to the invention.

The variants shown in FIGS. 2c and 2d differ from the embodiment shown in FIGS. 2a and 2b in terms of the number of the arc-shaped lines. In the variant shown in FIG. 2c, four arc-shaped lines 13a, 13b, 13c and 13d are provided, by means of which four segments 14a, 14b, 14c and 14d of different sizes can be separated from the wound dressing 1. In the variant shown in FIG. 2d there are even five arc-shaped lines 13a, 13b, 13c, 13d and 13e, by means of which five segments 14a, 14b, 14c, 14d and 14e of different sizes can be separated from the wound dressing 1. In both cases, the arc-shaped lines are each arranged approximately parallel to one another and at regular intervals from one another.

Figure 3:
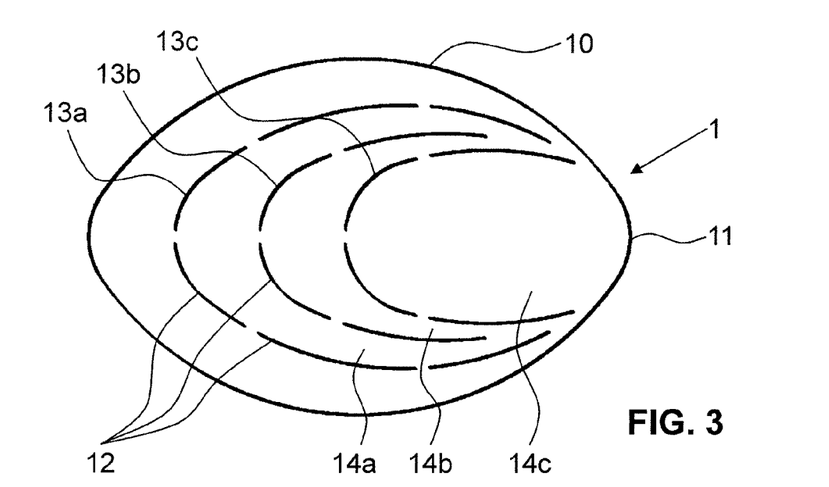
FIG. 3 shows a plan view of a wound dressing in a second embodiment according to the invention.

The embodiment shown in FIG. 3 differs from that of FIGS. 2a and 2b in that the arc-shaped lines 13a, 13b and 13c here extend symmetrically with respect to the major axis 7 and asymmetrically with respect to the minor axis 8. Their curvature is more pronounced by comparison with the embodiment in FIGS. 2a and 2b. Moreover, the arc-shaped lines 13a, 13b and 13c each have a greater length.

Figure 4:
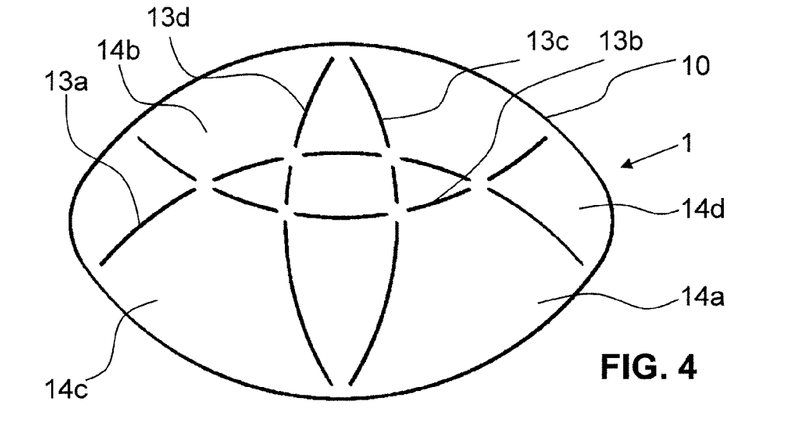
FIG. 4 shows a plan view of a wound dressing in a third embodiment according to the invention.

In the embodiment shown in FIG. 4, two arc-shaped lines 13a and 13b are provided which each extend asymmetrically with respect to the major axis 7 and symmetrically with respect to the minor axis 8, and which are curved in mutually opposite directions. While the arc-shaped line 13a extends approximately parallel to a portion of the outer edge 10 arranged at the top in FIG. 4, the arc-shaped line 13b extends to a portion of the outer edge 10 arranged at the bottom in FIG. 4 and lying diametrically opposite the aforementioned portion. The two arc-shaped lines 13a and 13b moreover intersect at two intersection points, which are arranged at a distance from the major axis 7.

The embodiment of FIG. 4 moreover has two further arc-shaped lines 13c and 13d which, in contrast to the arc-shaped lines 13a and 13b, each extend symmetrically with respect to the major axis 7 and asymmetrically with respect to the minor axis 8. The arc-shaped lines 13c and 13d are thus arranged at right angles to the arc-shaped lines 13a and 13b. The minor axis 8 extends centrally between the arc-shaped lines 13c and 13d, neither of which intersects the minor axis 8. Moreover, the arc-shaped lines 13c and 13d are curved in mutually opposite directions, without intersecting each other.

Since the arc-shaped lines 13a and 13b, on the one hand, and the arc-shaped lines 13c and 13d, on the other hand, are in each case curved in mutually opposite directions, each pair of lines delimits an additional segment that is separable from the wound dressing 1. The first additional segment is formed by the intersection of the segments 14a and 14b, and the second additional segment is formed by the intersection of the segments 14c and 14d. On account of the right-angled arrangement and the mutual curvatures of the arc-shaped lines 13a, 13b, 13c, 13d, many further segments are obtained which, for example, are formed by the intersections of the segments 14a and 14d or 14b and 14c. As is shown in FIG. 4, the bridge portions 15 here advantageously correspond exactly to the intersection points of the arc-shaped lines 13a, 13b, 13c, 13d.

Figure 5:
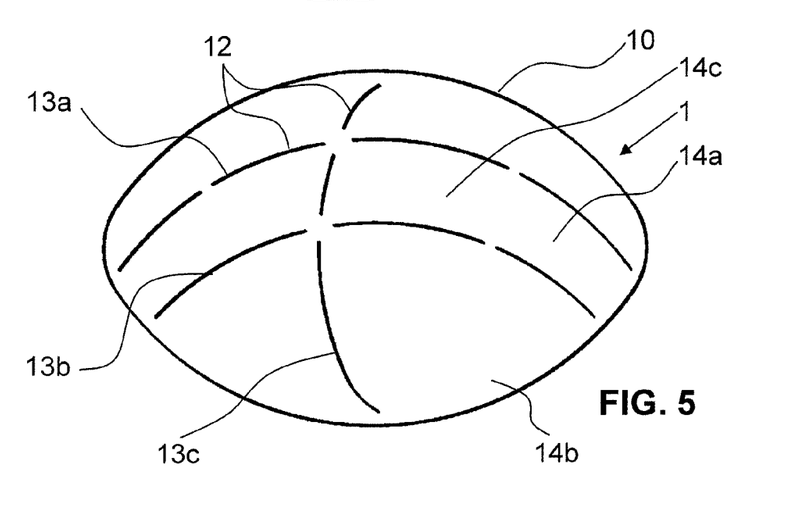
FIG. 5 shows a plan view of a wound dressing in a fourth embodiment according to the invention.

In the embodiment shown in FIG. 5, in contrast to the embodiment of FIG. 4, the two arc-shaped lines 13a and 13b are each curved in the same direction and extend at least approximately parallel to each other and also to the portion of the outer edge 10 arranged at the top in FIG. 5. Moreover, compared to the embodiment of FIG. 4, the arc-shaped line 13d extending symmetrically with respect to the major axis 7 is omitted.

Figure 6:
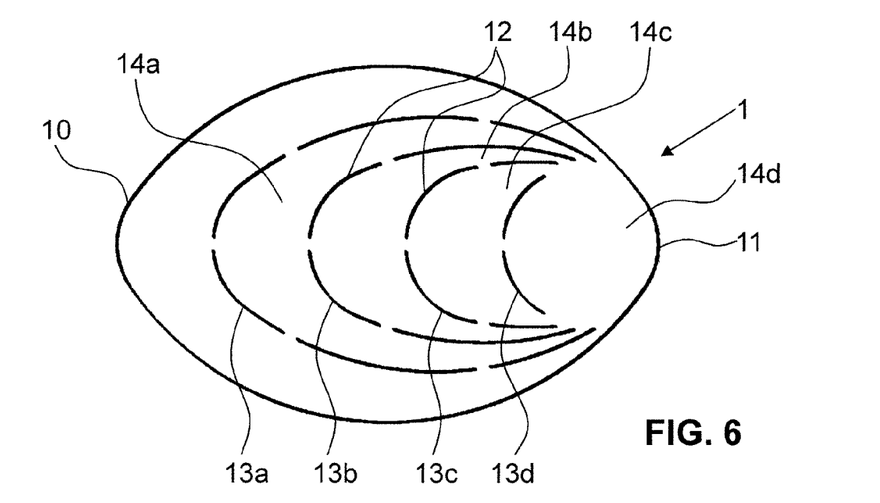
FIG. 6 shows a plan view of a wound dressing in a fifth embodiment according to the invention.
Figure 7:
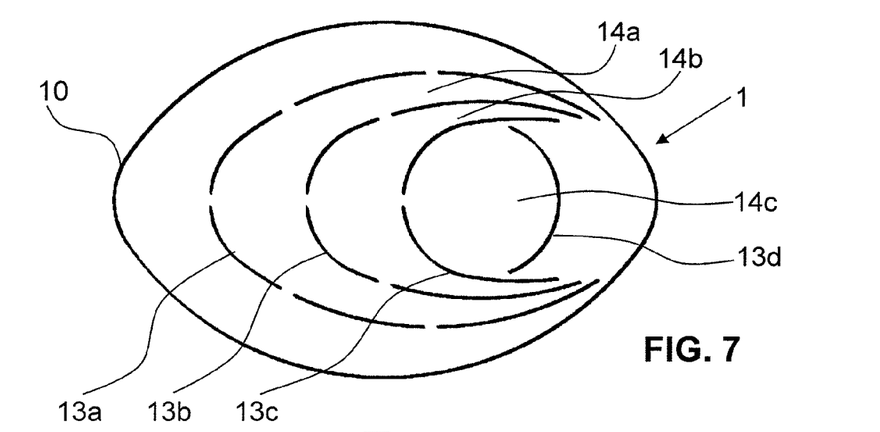
FIG. 7 shows a plan view of a wound dressing in a sixth embodiment according to the invention.

The embodiments shown in FIGS. 6 and 7 are similar to the embodiment of FIG. 3.

However, in contrast to the latter, in FIGS. 6 and 7 circular segments 14d and 14c are formed by the arc-shaped line 13d and the outer edge 10 and, respectively, by the arc-shaped lines 13c and 13d. It has been found that the circular shape is often advantageous in the case of wounds 20 that cover a fairly small area. In both embodiments in FIGS. 6 and 7, the segments 14a, 14b and 14c (and 14d in FIG. 6) merge continuously from a somewhat ellipsoid shape to a circular shape as their surface area decreases.

Figure 8A:
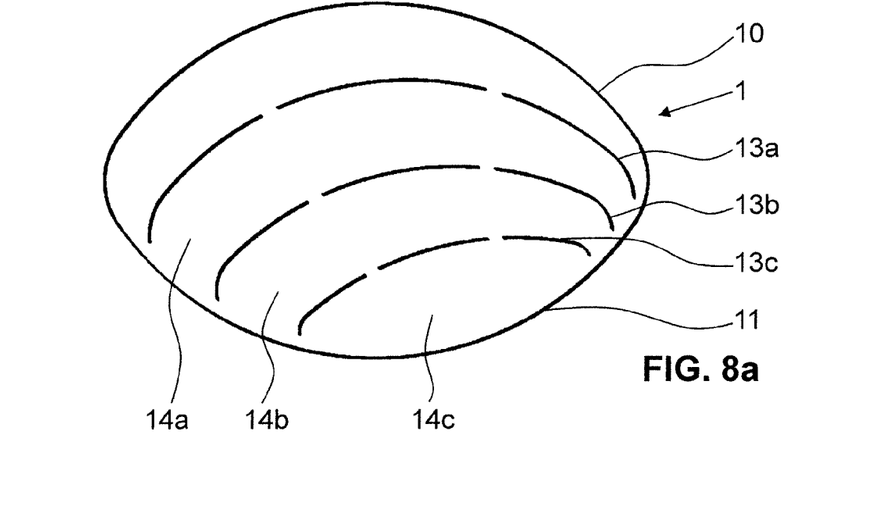
FIG. 8a shows a plan view of a wound dressing in a seventh embodiment according to the invention.
Figure 8B:
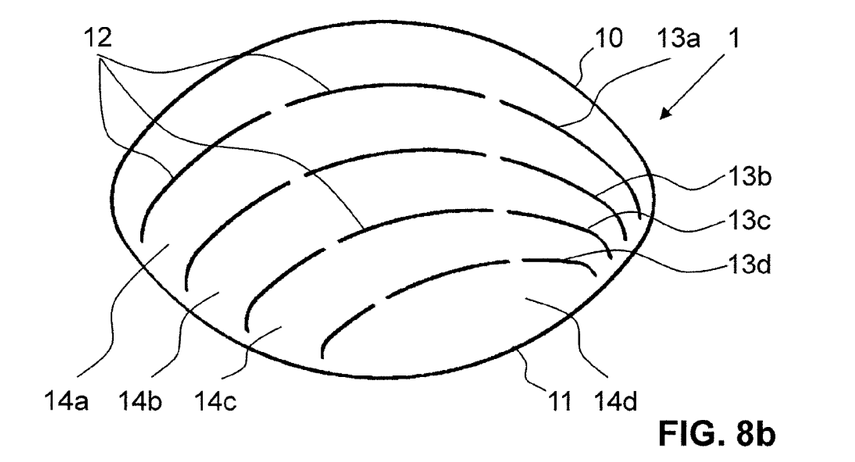
FIG. 8b shows a plan view of a wound dressing in a variant of the seventh embodiment according to the invention.

The embodiments shown in FIGS. 8a and 8b differ from those of FIGS. 2b and 2c in that the arc-shaped lines 13a, 13b, 13c and 13d each extend not only asymmetrically with respect to the major axis 7 but also slightly asymmetrically with respect to the minor axis 8. The asymmetry with respect to the minor axis 8 increases as the length of the arc-shaped lines 13a, 13b, 13c and 13d decreases. Thus, the shape of the segments 14a, 14b, 14c and 14d can accordingly be better adapted to the requirements as the surface area decreases. Here too, a mussel-shaped division of the wound dressing 1 can be clearly seen.

Figure 9:
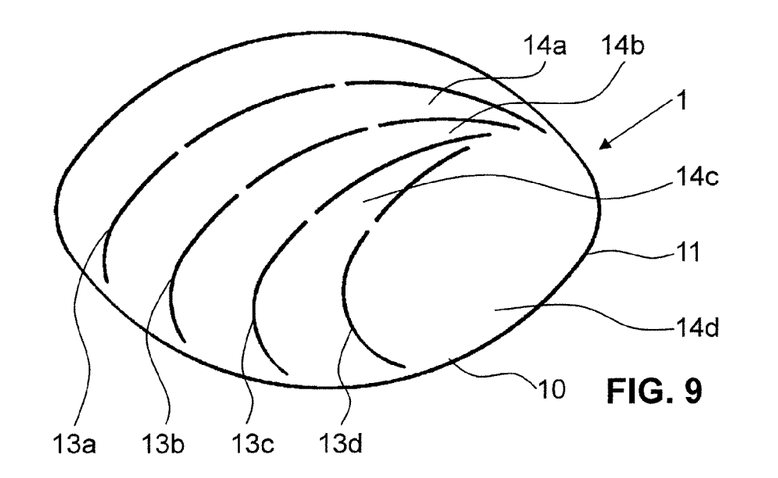
FIG. 9 shows a plan view of a wound dressing in an eighth embodiment according to the invention.

In the embodiment shown in FIG. 9, the increase in asymmetry as the surface area decreases with respect to the arc-shaped lines 13a, 13b, 13c and 13d delimiting the segments 14a, 14b, 14c and 14d is more pronounced than in FIG. 8b. As a result of the doubly asymmetrical arrangement of the arc-shaped lines 13a, 13b, 13c and 13d, the strongly curved portion of the outer edge 10, arranged at the far right in FIG. 9, can be still better utilized, and for all the segments 14a, 14b, 14c and 14d. It can be clearly seen that, as the surface area decreases, the substantially ellipsoid shape of the segments 14a, 14b, 14c and 14d at the opposite end areas initially tapers to a point and is then increasingly rounded and, finally (segment 14d), has an almost rectangular shape with rounded corners.

Figure 10:
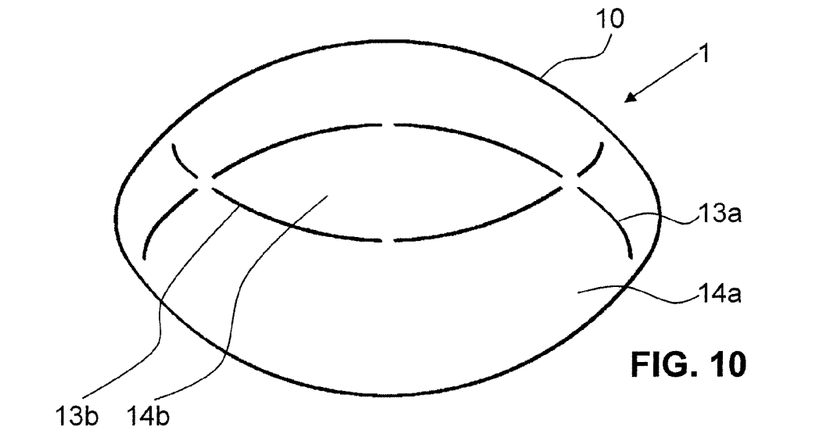
FIG. 10 shows a plan view of a wound dressing in a ninth embodiment according to the invention.

FIG. 10 shows a further embodiment in which the incisions 12 are arranged in the same way as in the embodiment of FIG. 4 and form arc-shaped lines 13a and 13b. Compared to the embodiment of FIG. 4, however, the arc-shaped lines 13c and 13d extending symmetrically with respect to the major axis 7 are omitted. Moreover, in contrast to FIG. 4, the arc-shaped lines 13a and 13b each have a curvature that increases towards the outer edge 10, such that the segments 14a and 14b, in terms of their shape, each correspond better to the shape of the overall wound dressing 1. Arc-shaped lines 13a-13e of this kind with curvatures increasing towards the outer edge can also be seen in the embodiments shown in FIGS. 2a-2d, 5, 8a, 8b.

Of course, the invention described here is not limited to the embodiments mentioned, and many modifications are possible. In particular, the embodiments shown in FIGS. 2a to 10 can be combined with one another in any desired way. For example, an individual wound dressing can also have a plurality of the patterns of arc-shaped lines shown in the embodiments of FIGS. 2a to 10 in combination with one another. One or more arc-shaped lines selected from different embodiments and variants can of course also be combined with one another in any desired way. Furthermore, the outer shape of the wound dressing can of course differ from the shape in the embodiments shown in FIGS. 2a to 10. Many other modifications are conceivable.

The invention claimed is:

1. A porous wound dressing for use in negative-pressure therapy of wounds, comprising
an outer edge which defines an oval outer shape of the wound dressing with a major axis and a minor axis,
one or more incisions or perforations which together form a plurality of arc-shaped lines and serve for cutting the wound dressing to size in order to adapt the wound dressing to the size of a wound,
wherein each of the arc-shaped lines extends asymmetrically with respect to the major axis and/or to the minor axis and encloses, together with a portion of the outer edge, a segment of the wound dressing that is designed for separation from the wound dressing and for subsequent use in the negative-pressure therapy of wounds,
wherein the segments, which in each case are enclosed by one of the arc-shaped lines and the respective portion of the outer edge, are each arranged asymmetrically with respect to the major axis and/or to the minor axis, and in each case have an oval outer shape which corresponds to the oval outer shape of the wound dressing, such that an observer is able to readily recognize the oval outer shape of the wound dressing in the oval outer shape of the segment, and
wherein the arc-shaped lines are arranged at regular intervals from one another and extend at least approximately parallel to one another and to a further portion of the outer edge of the wound dressing, such that a mussel-shaped division of the wound dressing into the segments is obtained.

2. The wound dressing according to claim 1, wherein bridge portions are provided which are each arranged between the incisions or perforations in order to separate these from one another within the respective arc-shaped line, or which are each arranged at the end points of the arc-shaped lines, in order to separate the latter there from the outer edge of the wound dressing.

3. The wound dressing according to claim 2, wherein the bridge portions are each arranged at regular intervals along the arc-shaped lines.

4. The wound dressing according to claim 1, wherein the arc-shaped lines each extend from a first part of the outer edge of the wound dressing as far as a second part of the outer edge of the wound dressing.

5. The wound dressing according to claim 1, wherein the arc-shaped lines each extend asymmetrically with respect to the major axis and intersect the minor axis, or they extend asymmetrically with respect to the minor axis and intersect the major axis.

6. The wound dressing according to claim 1, wherein the arc-shaped lines each extend symmetrically with respect to the minor axis or to the major axis.

7. The wound dressing according to claim 6, wherein at least one of the arc-shaped lines extends symmetrically with respect to the minor axis or to the major axis, and wherein a further arc-shaped line formed by one or more incisions or perforations is provided which extends symmetrically with respect to the minor axis or to the major axis and extends at least approximately parallel to a yet further portion of the outer edge of the wound dressing, which yet further portion lies radially opposite the further portion.

8. The wound dressing according to claim 1, wherein at least one of the arc-shaped lines extends symmetrically with respect to the minor axis, and wherein at least one further arc-shaped line formed by one or more incisions or perforations is provided which extends symmetrically with respect to the major axis.

9. The wound dressing according to claim 1, wherein the arc-shaped lines each extend asymmetrically with respect to the major axis and also asymmetrically with respect to the minor axis.

10. The wound cover kit for use in negative-pressure therapy of wounds, having
a wound-side contact sheet designed to be placed directly on a wound;
a covering which serves to cover and seal off the wound area from the outside; and
a porous wound dressing comprising
an outer edge which defines an oval outer shape of the wound dressing with a major axis and a minor axis,
one or more incisions or perforations which together form a plurality of arc-shaped lines and serve for cutting the wound dressing to size in order to adapt the wound dressing to the size of a wound,
wherein each of the arc-shaped lines extends asymmetrically with respect to the major axis and/or to the minor axis and encloses, together with a portion of the outer edge, a segment of the wound dressing that is designed for separation from the wound dressing and for subsequent use in the negative-pressure therapy of wounds,
wherein the segments, which in each case are enclosed by one of the arc-shaped lines and the respective portion of the outer edge, are each arranged asymmetrically with respect to the major axis and/or to the minor axis,
and in each case have an oval outer shape which corresponds to the oval outer shape of the wound dressing, such that an observer is able to readily recognize the oval outer shape of the wound dressing in the oval outer shape of the segment or segments, and
wherein the arc-shaped lines are arranged at regular intervals from one another and extend at least approximately parallel to one another and to a further portion of the outer edge of the wound dressing, such that a mussel-shaped division of the wound dressing into the segments is obtained.

11. The wound dressing according to claim 1, wherein the wound dressing serves for the treatment of abdominal wounds.

12. The wound dressing according to claim 1, wherein the incisions or perforations in each case extend all the way through the wound dressing.

13. The wound dressing according to claim 1, wherein the wound dressing is made from an open-cell, reticulated foam.

14. The wound dressing according to claim 1, wherein the wound dressing is liquid-permeable at least in one direction.

15. The wound dressing according to claim 2, wherein the wound dressing has a reduced thickness at the bridge portions.

16. The wound dressing according to claim 1, wherein the oval outer shapes of the segments in each case correspond such to the oval outer shape of the wound dressing, that the wound dressing can in each case be overlaid with the segment, if their dimensioning is suitably adapted without changing the aspect ratios, such that at least 80% of the surface areas of the respective segment and of the wound dressing in its original shape and dimension overlap each other.

17. The wound dressing according to claim 1, wherein the oval outer shapes of the segments in each case correspond such to the oval outer shape of the wound dressing, that the wound dressing can in each case be overlaid with the segment, if their dimensioning is suitably adapted without changing the aspect ratios, such that at least 90% of the surface areas of the respective segment and of the wound dressing in its original shape and dimension overlap each other.

* * * * *